(12) United States Patent
Bahn et al.

(10) Patent No.: US 7,838,246 B2
(45) Date of Patent: Nov. 23, 2010

(54) BIOMARKERS FOR SCHIZOPHRENIA

(75) Inventors: Sabine Bahn, Cambridgeshire (GB); Jeffrey Huang, Cambridgeshire (GB)

(73) Assignee: Psynova Neurotech Limited, Cambridge (GB)

( * ) Notice: Subject to any disclaimer, the term of this patent is extended or adjusted under 35 U.S.C. 154(b) by 0 days.

(21) Appl. No.: 11/813,122

(22) PCT Filed: Feb. 14, 2006

(86) PCT No.: PCT/GB2006/050034

§ 371 (c)(1),
(2), (4) Date: Jan. 27, 2009

(87) PCT Pub. No.: WO2006/085121

PCT Pub. Date: Aug. 17, 2006

(65) Prior Publication Data

US 2010/0003694 A1 Jan. 7, 2010

(30) Foreign Application Priority Data

Feb. 14, 2005 (GB) ................ 0502979.8

(51) Int. Cl.
*G01N 33/53* (2006.01)
*G01N 33/537* (2006.01)
*G01N 33/566* (2006.01)
*G01N 25/18* (2006.01)

(52) U.S. Cl. .............. 435/7.1; 435/7.8; 435/7.92; 436/501; 436/503; 436/149

(58) Field of Classification Search ............. None
See application file for complete search history.

(56) References Cited

FOREIGN PATENT DOCUMENTS

WO    WO 02/082075 A    10/2002

OTHER PUBLICATIONS

Bahn, S., "Functional genomics studies of schizophrenia and bipolar disorder," *International Journal of Neuropsychopharmacology*, Jun. 2004, vol. 7, No. Suppl. 1, p. S11.
Berry, Neeraj, et al., "Molecular genetics of schizophrenia: A critical review," *Journal of Psychiatry & Neuroscience*, Nov. 2003, vol. 28, No. 6, pp. 415-429.
Carrette, O. et al., "A panel of cerebrospinal fluid potential biomarkers for the diagnosis of Alzheimer's disease," *Proteomics*, Wiley-VCH Verlag, Weinheim, DE, Aug. 2003, vol. 3, No. 8, pp. 1486-1494.
Miyatake, Y., et al., "The signal transduction pathway for VGF expression due to NGF is different from that due to BFGF in PC12H cell," *Biochemistry and Molecular Biology International*, Academic Press, London, GB, Jun. 1993, vol. 30, No. 2, pp. 231-236.
Vercauteren et al., "Proteomic approaches in brain research and neuropharmacology," *European Journal of Pharmacology*, Amsterdam, NL, Oct. 1, 2004, vol. 500, No. 1-3, pp. 385-398.
Yuan, Xianglin, et al., "Human cerebrospinal fluid peptidomics," *Journal of Mass Spectrometry*, Feb. 2005, vol. 40, No. 2, pp. 176-181.

*Primary Examiner*—Olga N Chernyshev
(74) *Attorney, Agent, or Firm*—Saliwanchik, Lloyd & Saliwanchik

(57) ABSTRACT

The present invention provides biomarkers for schizophrenic and bipolar disorders and methods of diagnosis, monitoring and screening associated with the biomarkers and kits for performing such methods.

10 Claims, 4 Drawing Sheets

A <ins>Signal peptide</ins>

MKALRLSASALFCLLLINGLGAAPPGRPEAQPPPLSSEHKEPVAGDAVPG
PKDGSAPEVRGARNSEPQDEGELFQGVDPRALAAVLLQALDRPASPPAPS
GSQQGPEEEAAEALLTETVRSQTHSLPAAGEPEPAAPPRPQTPENGPEAS
DPSEELEALASLLQELRDFSPSSAKRQQETAAAETETRTHTLTRVNLESP
GPERVWRASWGEFQARVPERAPLPPPAPSQFQARMPDSGPLPETHKFGEG
VSSPKTHLGEALAPLSKAYQGVAAPFPKARRAESALLGGSEAGERLLQQG
LAQVEAGRRQAEATRQAAAQEERLADLASDLLLQYLLQGGARQRGLGGRG
LQEAAEERESAREEEAEQERRGGEERVGEEDEEAAEAAEAEADEAERAR
QNALLFAEEEDGEAGAEDKRSQEETPGHRRKEAEGTEEGGEEEDDEEMDP
QTIDSLIELSTKLHLPADDVVSIIEEVEEKRNRKKKAPPEPVPPPRAAPA
PTHVRSPQPPPPPPSARDELPDWNEVLPPWDREEDEVYPPGPYHPFPNYI
RPRTLQPPSALRRRHYHHALPPSRHYPGREAQARHAQQEEAEAEERRLQE
QEELENYIEHVLLRRP

B
Peak at 3.96 kDa    APPGRPEAQPPPLSSEHKEPVAGDAVPGPKDGSAPEVR
Peak at 3.69 kDa    ---GRPEAQPPPLSSEHKEPVAGDAVPGPKDGSAPEVR

Figure 3

SEQUENCE LISTING

```
<160> NUMBER OF SEQ ID NOS: 3

<210> SEQ ID NO 1
<211> LENGTH: 38
<212> TYPE: PRT
<213> ORGANISM: Human

<400> SEQUENCE: 1

Ala Pro Pro Gly Arg Pro Glu Ala Gln Pro Pro Leu Ser Ser Glu
1               5                   10                  15

His Lys Glu Pro Val Ala Gly Asp Ala Val Pro Gly Pro Lys Asp Gly
            20                  25                  30

Ser Ala Pro Glu Val Arg
        35

<210> SEQ ID NO 2
<211> LENGTH: 616
<212> TYPE: PRT
<213> ORGANISM: Human

<400> SEQUENCE: 2

Met Lys Ala Leu Arg Leu Ser Ala Ser Ala Leu Phe Cys Leu Leu Leu
1               5                   10                  15

Ile Asn Gly Leu Gly Ala Ala Pro Pro Gly Arg Pro Glu Ala Gln Pro
            20                  25                  30

Pro Pro Leu Ser Ser Glu His Lys Glu Pro Val Ala Gly Asp Ala Val
        35                  40                  45

Pro Gly Pro Lys Asp Gly Ser Ala Pro Glu Val Arg Gly Ala Arg Asn
    50                  55                  60

Ser Glu Pro Gln Asp Glu Gly Glu Leu Phe Gln Gly Val Asp Pro Arg
65                  70                  75                  80

Ala Leu Ala Ala Val Leu Leu Gln Ala Leu Asp Arg Pro Ala Ser Pro
                85                  90                  95

Pro Ala Pro Ser Gly Ser Gln Gln Gly Pro Glu Glu Glu Ala Ala Glu
            100                 105                 110
```

```
Ala Leu Leu Thr Glu Thr Val Arg Ser Gln Thr His Ser Leu Pro Ala
        115                 120                 125

Ala Gly Glu Pro Glu Pro Ala Ala Pro Pro Arg Pro Gln Thr Pro Glu
        130                 135                 140

Asn Gly Pro Glu Ala Ser Asp Pro Ser Glu Leu Glu Ala Leu Ala
145                 150                 155                 160

Ser Leu Leu Gln Glu Leu Arg Asp Phe Ser Pro Ser Ser Ala Lys Arg
                165                 170                 175

Gln Gln Glu Thr Ala Ala Ala Glu Thr Glu Thr Arg Thr His Thr Leu
                180                 185                 190

Thr Arg Val Asn Leu Glu Ser Pro Gly Pro Glu Arg Val Trp Arg Ala
        195                 200                 205

Ser Trp Gly Glu Phe Gln Ala Arg Val Pro Glu Arg Ala Pro Leu Pro
        210                 215                 220

Pro Pro Ala Pro Ser Gln Phe Gln Ala Arg Met Pro Asp Ser Gly Pro
225                 230                 235                 240

Leu Pro Glu Thr His Lys Phe Gly Glu Gly Val Ser Ser Pro Lys Thr
                245                 250                 255

His Leu Gly Glu Ala Leu Ala Pro Leu Ser Lys Ala Tyr Gln Gly Val
        260                 265                 270

Ala Ala Pro Phe Pro Lys Ala Arg Arg Ala Glu Ser Ala Leu Leu Gly
        275                 280                 285

Gly Ser Glu Ala Gly Glu Arg Leu Leu Gln Gln Gly Leu Ala Gln Val
        290                 295                 300

Glu Ala Gly Arg Arg Gln Ala Glu Ala Thr Arg Gln Ala Ala Ala Gln
305                 310                 315                 320

Glu Glu Arg Leu Ala Asp Leu Ala Ser Asp Leu Leu Leu Gln Tyr Leu
                325                 330                 335

Leu Gln Gly Gly Ala Arg Gln Arg Gly Leu Gly Gly Arg Gly Leu Gln
        340                 345                 350

Glu Ala Ala Glu Glu Arg Glu Ser Ala Arg Glu Glu Glu Ala Glu
        355                 360                 365

Gln Glu Arg Arg Gly Gly Glu Arg Val Gly Glu Glu Asp Glu Glu
        370                 375                 380

Ala Ala Glu Ala Ala Glu Ala Glu Ala Asp Glu Ala Glu Arg Ala Arg
385                 390                 395                 400

Gln Asn Ala Leu Leu Phe Ala Glu Glu Glu Asp Gly Glu Ala Gly Ala
                405                 410                 415

Glu Asp Lys Arg Ser Gln Glu Glu Thr Pro Gly His Arg Arg Lys Glu
                420                 425                 430

Ala Glu Gly Thr Glu Glu Gly Gly Glu Glu Asp Asp Glu Glu Met
        435                 440                 445

Asp Pro Gln Thr Ile Asp Ser Leu Ile Glu Leu Ser Thr Lys Leu His
        450                 455                 460

Leu Pro Ala Asp Asp Val Val Ser Ile Ile Glu Glu Val Glu Glu Lys
465                 470                 475                 480

Arg Asn Arg Lys Lys Ala Pro Pro Glu Pro Val Pro Pro Pro Arg
                485                 490                 495

Ala Ala Pro Ala Pro Thr His Val Arg Ser Pro Gln Pro Pro Pro
                500                 505                 510

Pro Pro Ser Ala Arg Asp Glu Leu Pro Asp Trp Asn Glu Val Leu Pro
                515                 520                 525

Pro Trp Asp Arg Glu Glu Asp Glu Val Tyr Pro Pro Gly Pro Tyr His
```

-continued

```
               530                 535                 540

Pro Phe Pro Asn Tyr Ile Arg Pro Arg Thr Leu Gln Pro Pro Ser Ala
545                 550                 555                 560

Leu Arg Arg Arg His Tyr His His Ala Leu Pro Pro Ser Arg His Tyr
                565                 570                 575

Pro Gly Arg Glu Ala Gln Ala Arg His Ala Gln Gln Glu Glu Ala Glu
            580                 585                 590

Ala Glu Glu Arg Arg Leu Gln Glu Gln Glu Glu Leu Glu Asn Tyr Ile
        595                 600                 605

Glu His Val Leu Leu Arg Arg Pro
    610                 615

<210> SEQ ID NO 3
<211> LENGTH: 35
<212> TYPE: PRT
<213> ORGANISM: Human

<400> SEQUENCE: 3

Gly Arg Pro Glu Ala Gln Pro Pro Leu Ser Ser Glu His Lys Glu
1               5                   10                  15

Pro Val Ala Gly Asp Ala Val Pro Gly Pro Lys Asp Gly Ser Ala Pro
                20                  25                  30

Glu Val Arg
        35
```

BIOMARKERS FOR SCHIZOPHRENIA

This application is a National Stage Application of International Application Number PCT/GB2006/050034, filed Feb. 14, 2006, which claims priority to Great Britain Application No. 0502979.8, filed Feb. 14, 2005.

FIELD OF THE INVENTION

The present invention relates to peptide biomarkers for schizophrenic disorders and for bipolar disorders, and to uses of the biomarkers, in particular in methods of diagnosis or of monitoring a schizophrenic disorder or bipolar disorder, or predisposition thereto. Biomarkers and methods in which they are employed can be used to assist diagnosis to confirm the existence of a schizophrenic or bipolar disorder, or to assess onset and development of a schizophrenic or bipolar disorder. The invention also relates to use of biomarkers in clinical screening, assessment of prognosis, evaluation of therapy, and for drug screening and drug development in the field of schizophrenic and/or bipolar disorders.

BACKGROUND TO THE INVENTION

Schizophrenia is a major psychiatric disorder affecting up to 1% of the population. It is found at similar prevalence in both sexes and is found throughout diverse cultures and geographic areas (1; 2). The World Health Organization found schizophrenia to be the world's fourth leading cause of disability (3; 4) that accounts for 1.1% of the total DALYs (Disability Adjusted Life Years) and 2.8% of YLDs (years of life lived with disability)(4). It was estimated that the economic cost of schizophrenia exceeded US$ 19 billion in 1991, more than the total cost of all cancers in the United States. Effective treatments used early in the course of schizophrenia can improve prognosis and help reduce the costs associated with this illness.

The clinical syndrome of schizophrenia comprises discrete clinical features including positive symptoms (hallucination, delusions, disorganization of thought and bizarre behaviour); negative symptoms (loss of motivation, restricted range of emotional experience and expression and reduced hedonic capacity); and cognitive impairments with extensive variation between individuals (5). No single symptom is unique to schizophrenia and/or is present in every case. Despite the lack of homogeneity of clinical symptoms, the current diagnosis and classification of schizophrenia is still based on the clinical symptoms presented by a patient (6). This is primarily because the aetiology of schizophrenia remains unknown (in fact, the aetiology of most psychiatric diseases is still unclear) and classification based on aetiology is as yet not feasible. However, the clinical symptoms of schizophrenia are often similar to symptoms observed in other neuropsychiatric disorders, making accurate diagnosis difficult.

Due to the complex spectrum of symptoms presented by subjects with schizophrenic disorders and their similarity to other mental disorders, current diagnosis of schizophrenia is made on the basis of a complicated clinical examination/interview of the patient's family history, personal history, current symptoms (mental state examination) and the presence/absence of other disorders (differential diagnosis; Table 1). This assessment allows a "most likely" diagnosis to be established, leading to the initial treatment plan. To be diagnosed with schizophrenia, a patient (with few exceptions) should have psychotic, "loss-of-reality" symptoms for at least six months (DSM IV) and show increasing difficulty in functioning normally.

The ICD-10 Classification of Mental and Behavioural Disorders, published by the World Health Organization in 1992, is the manual most commonly used by European psychiatrists to diagnose mental health conditions including schizophrenia and bipolar disorder. The manual provides detailed diagnostic guidelines and defines the various forms of schizophrenia: schizophrenia, paranoid schizophrenia, hebrephrenic schizophrenia, catatonic schizophrenia, undifferentiated schizophrenia, post-schizophrenic schizophrenia, residual schizophrenia and simple schizophrenia.

The Diagnostic and Statistical Manual of Mental Disorders fourth edition (DSM IV) published by the American Psychiatric Association, Washington D.C., 1994, has proven to be an authoritative reference handbook for health professionals both in the United Kingdom and in the United States in categorizing and diagnosing mental health problems. This describes the diagnostic criteria, subtypes, associated features and criteria for differential diagnosis of mental health disorders, including schizophrenia and bipolar disorder.

DSM IV Diagnostic Criteria for Schizophrenia

A. Characteristic symptoms: Two (or more) of the following, each present for a significant portion of time during a 1-month period (or less if successfully treated): delusions, hallucinations, disorganized speech (e.g., frequent derailment or incoherence), grossly disorganized or catatonic behavior, negative symptoms, i.e., affective flattening, alogia, or avolition. Only one Criterion A symptom is required if delusions are bizarre or hallucinations consist of a voice keeping up a running commentary on the person's behavior or thoughts, or two or more voices conversing with each other.

B. Social/occupational dysfunction: For a significant portion of the time since the onset of the disturbance, one or more major areas of functioning such as work, interpersonal relations, or self-care are markedly below the level achieved prior to the onset (or when the onset is in childhood or adolescence, failure to achieve expected level of interpersonal, academic, or occupational achievement).

C. Duration: Continuous signs of the disturbance persist for at least 6 months. This 6-month period must include at least 1 month of symptoms (or less if successfully treated) that meet Criterion A (i.e., active-phase symptoms) and may include periods of prodromal or residual symptoms. During these prodromal or residual periods, the signs of the disturbance may be manifested by only negative symptoms or two or more symptoms listed in Criterion A present in an attenuated form (e.g., odd beliefs, unusual perceptual experiences).

D. Schizoaffective and Mood Disorder exclusion: Schizoaffective Disorder and Mood Disorder With Psychotic Features have been ruled out because either (1) no Major Depressive Episode, Manic Episode, or Mixed Episode have occurred concurrently with the active-phase symptoms; or (2) if mood episodes have occurred during active-phase symptoms, their total duration has been brief relative to the duration of the active and residual periods.

E. Substance/general medical condition exclusion: The disturbance is not due to the direct physiological effects of a substance (e.g., a drug of abuse, a medication) or a general medical condition.

F. Relationship to a Pervasive Developmental Disorder: If there is a history of Autistic Disorder or another Pervasive Developmental Disorder, the additional diagnosis of Schizophrenia is made only if prominent delusions or hallucinations are also present for at least a month (or less if successfully treated).

Schizophrenia Subtypes

1. Paranoid Type: A type of Schizophrenia in which the following criteria are met: Preoccupation with one or more delusions or frequent auditory hallucinations. None of the following is prominent: disorganized speech, disorganized or catatonic behavior, or flat or inappropriate affect.

2. Catatonic Type: A type of Schizophrenia in which the clinical picture is dominated by at least two of the following: motoric immobility as evidenced by catalepsy (including waxy flexibility) or stupor, excessive motor activity (that is apparently purposeless and not influenced by external stimuli), extreme negativism (an apparently motiveless resistance to all instructions or maintenance of a rigid posture against attempts to be moved) or mutism, peculiarities of voluntary movement as evidenced by posturing (voluntary assumption of inappropriate or bizarre postures), stereotyped movements, prominent mannerisms, or prominent grimacing, echolalia or echopraxia.

3. Disorganized Type: A type of Schizophrenia in which the following criteria are met: all of the following are prominent: disorganized speech, disorganized behavior, flat or inappropriate affect. The criteria are not met for Catatonic Type.

4. Undifferentiated Type: A type of Schizophrenia in which symptoms that meet Criterion A are present, but the criteria are not met for the Paranoid, Disorganized, or Catatonic Type.

5. Residual Type: A type of Schizophrenia in which the following criteria are met: Absence of prominent delusions, hallucinations, disorganized speech, and grossly disorganized or catatonic behavior. There is continuing evidence of the disturbance, as indicated by the presence of negative symptoms or two or more symptoms listed in Criterion A for Schizophrenia, present in an attenuated form (e.g., odd beliefs, unusual perceptual experiences).

Schizophrenia Associated Features

Features associated with schizophrenia include: learning problems, hypoactivity, psychosis, euphoric mood, depressed mood, somatic or sexual dysfunction, hyperactivity, guilt or obsession, sexually deviant behavior, odd/eccentric or suspicious personality, anxious or fearful or dependent personality, dramatic or erratic or antisocial personality.

Differential Diagnosis of Schizophrenia

Many disorders have similar or even the same symptoms as schizophrenia. The clinician, therefore, in his/her diagnostic attempt has to differentiate against the following disorders which he/she needs to rule out to establish a precise diagnosis: psychotic disorder due to a general medical condition, delirium, or dementia; substance-induced psychotic disorder; substance-induced delirium; substance-induced persisting dementia; substance-related disorders; mood disorder with psychotic features; schizoaffective disorder; depressive disorder not otherwise specified; bipolar disorder not otherwise specified; mood disorder with catatonic features; schizophreniform disorder; brief psychotic disorder; delusional disorder; psychotic disorder not otherwise specified; pervasive developmental disorders (e.g., autistic disorder); childhood presentations combining disorganized speech (from a communication disorder) and disorganized behavior (from attention-deficit/hyperactivity disorder); schizotypal disorder; schizoid personality disorder and paranoid personality disorder.

DSM IV Diagnostic Categories for Manic Depression/Bi-Polar Affective Disorder (BD)

Only two sub-types of bipolar illness have been defined clearly enough to be given their own DSM categories, Bipolar I and Bipolar II.

Bipolar I: This disorder is characterized by manic episodes; the 'high' of the manic-depressive cycle. Generally this manic period is followed by a period of depression, although some bipolar I individuals may not experience a major depressive episode. Mixed states, where both manic or hypomanic symptoms and depressive symptoms occur at the same time, also occur frequently with bipolar I patients (for example, depression with the racing thoughts of mania). Also, dysphoric mania is common, this is mania characterized by anger and irritability.

Bipolar II: This disorder is characterized by major depressive episodes alternating with episodes of hypomania, a milder form of mania. Hypomanic episodes can be a less disruptive form of mania and may be characterized by low-level, non-psychotic symptoms of mania, such as increased energy or a more elated mood than usual. It may not affect an individual's ability to function on a day to day basis. The criteria for hypomania differ from those for mania only by their shorter duration (at least 4 days instead of 1 week) and milder severity (no marked impairment of functioning, hospitalization or psychotic features).

If the depressive and manic symptoms last for two years and do not meet the criteria for a major depressive or a manic episode then the diagnosis is classified as a Cyclothymic disorder, which is a less severe form of bipolar affective disorder. Cyclothymic disorder is diagnosed over the course of two years and is characterized by frequent short periods of hypomania and depressive symptoms separated by periods of stability.

Rapid cycling occurs when an individual's mood fluctuates from depression to hypomania or mania in rapid succession with little or no periods of stability in between. One is said to experience rapid cycling when one has had four or more episodes in a given year that meet criteria for major depressive, manic, mixed or hypomanic episodes. Some people who rapid cycle can experience monthly, weekly or even daily shifts in polarity (sometimes called ultra rapid cycling).

When symptoms of mania, depression, mixed mood, or hypomania are caused directly by a medical disorder, such as thyroid disease or a stroke, the current diagnosis is Mood Disorder Due to a General Medical Condition, If a manic mood is brought about through an antidepressant, ECT or through an individual using street drugs, the diagnosis is Substance-induced Mood Disorder, with Manic Features.

Diagnosis of Bipolar III has been used to categorise manic episodes which occur as a result of taking an antidepressant medication, rather than occurring spontaneously. Confusingly, it has also been used in instances where an individual experiences hypomania or cyclothymia (i.e. less severe mania) without major depression.

Mania

Manic Depression is comprised of two distinct and opposite states of mood, whereby depression alternates with mania. The DSM IV gives a number of criteria that must be met before a disorder is classified as mania. The first one is that an individual's mood must be elevated, expansive or irritable. The mood must be a different one to the individual's usual affective state during a period of stability. There must be a marked change over a significant period of time. The person must become very elevated and have grandiose ideas. They may also become very irritated and may well appear to be 'arrogant' in manner. The second main criterion for mania emphasizes that at least three of the following symptoms must have been present to a significant degree: inflated sense of self importance, decreased need for sleep, increased talkativeness, flight of ideas or racing thoughts, easily distracted, increased goal-directed activity, excessive involvement in activities that can bring pleasure but may have disastrous consequences (e.g. sexual affairs and spending excessively). The third criterion for mania in the DSM IV emphasizes that the change in mood must be marked enough to affect an individual's job performance or ability to take part in regular social activities or relationships with others. This third criterion is used to emphasize the difference between mania and hypomania.

Depression

The DSM IV states that there are a number of criteria by which major depression is clinically defined. The condition must have been evident for at least two weeks and must have five of the following symptoms: a depressed mood for most of the day, almost every day, a loss of interest or pleasure in almost all activities, almost every day, changes in weight and appetite, sleep disturbance, a decrease in physical activity, fatigue and loss of energy, feelings of worthlessness or excessive feelings of guilt, poor concentration levels, suicidal thoughts.

Both the depressed mood and a loss of interest in everyday activities must be evident as two of the five symptoms which characterize a major depression. It is difficult to distinguish the symptoms of an individual suffering from the depressed mood of manic depression from those of someone suffering from a major depression. Dysthymia is a less severe depression than unipolar depression, but it can be more persistent.

Psychosis

Psychosis is characterized by disorders in basic perceptual, cognitive, affective, and judgmental processes. For example, one might experience delusions, hallucinations, disorganized speech, disorganized behaviour etc. A diagnosis of bipolar affective disorder does not mean that an individual will necessarily experience psychosis. Psychotic symptoms are associated with several different brain disorders, including lesions in the brain resulting from head traumas, strokes, tumours, infections or the use of illegal drugs. Psychotic symptoms may develop in serious depression.

Schizoaffective Disorder

Schizo-affective disorder is characterised by elements of both schizophrenia and bipolar disorder, it has been referred to as "schizophrenia with a mood component". Schizoaffective disorder is characterised by concomitant symptoms of both schizophrenia and bipolar disorder to a similar degree in a given episode of illness, thus it is generally very difficult to distinguish schizoaffective disorder from bipolar disorder or schizophrenia, and the existence of schizoaffective disorder as a distinct syndrome is a controversial subject in the field. There is often a failure to diagnose schizoaffective disorder because of the complex nature of the illness. Many individuals with schizoaffective disorder are originally diagnosed with manic depression.

Schizoid personality, schizophreniform disorder, schizotypal personality and bipolar disorder (manic depression) are frequently confused and misdiagnosed. Thus, a differential diagnosis is needed to distinguish schizophrenia and bipolar disorder from other conditions that present with similar symptoms, for example schizoaffective disorder, and brief psychotic disorder (6).

Individuals with bipolar disorder meet the full diagnostic criteria for schizophrenia in 20 to 30% of cases. Those with bipolar disorder are not always in either a manic or a depressive phase; there may be long periods during which they seem virtually symptom-free and do not present disordered thinking, delusions, voices, or other symptoms that characterise psychotic disorders per se. In bipolar disorder, an individual may not always be symptomatic, but during an episode, psychotic schizophrenia-like symptoms are found in the context of mania or depression, these symptoms include delusions of grandeur, hallucinations, wild optimism, grandiose behaviour, as well as physiological abnormalities in the form of a reduced need for sleep, increased appetite, libido and general drive and motivation.

The main distinguishing difference between bipolar disorder and major clinical depression is that in bipolar disorder, manic episodes occur. The existence of one manic episode (meeting DSM IV criteria) is sufficient to make a diagnosis of bipolar disorder. Distinguishing between bipolar disorder and depression is essential for assigning treatment; while depression is treated primarily with anti-depressant medication, bipolar disorder requires a mood-stabilizing medication such as lithium or valproate. Use of anti-depressants in bipolar disorder can sometimes trigger manic episodes.

It can take 6 months or more to make a definitive diagnosis of bipolar disorder, a schizophrenic disorder or other psychosis, because although the symptoms may be evident, it is often difficult to ascertain whether or not the symptoms are being caused by some other neuropsychiatric, neurodegenerative or neurodevelopmental disorder.

There is a need for diagnostic methods and tools that enable schizophrenic conditions and bipolar disorder to be distinguished from other disorders which present with similar symptoms. Differential diagnosis is also needed to exclude psychoses in the context of neurodegenerative and neurodevelopmental disorders as well as organic causes of psychoses, like epileptic and drug-induced psychoses.

The prolonged process currently needed to achieve accurate diagnosis may cause delay of appropriate treatment, which is likely to have serious implications for medium to long-term disease outcome (5; 7; 8). The development of objective diagnostic methods, tests and tools is urgently required to help distinguish between psychiatric diseases with similar clinical symptoms. Objective diagnostic methods, tests for schizophrenia and/or bipolar disorder will assist in monitoring individuals over the course of illness (treatment response, compliance etc.) and may also be useful in determining prognosis, as well as providing tools for drug screening and drug development.

Unfortunately, at present there is no standard, sensitive, specific test for schizophrenia or bipolar disorders.

One biochemical test currently under development for schizophrenia diagnosis is the niacin skin flush test (9-11), based on the observation that there is failure to respond to the niacin skin test in some schizophrenia patients, due to abnormal arachidonic acid metabolism (10). However, the specificity and sensitivity of this test shows an extreme inconsistency between studies, ranging from 23% to 87% (12-15), suggesting that the reliability and validity of this test still need to be verified.

International Patent Application Publication No. WO 01/63294 describes methods and compositions for screening, diagnosis, and determining prognosis of neuropsychiatric or neurological conditions (including BAD (bipolar affective disorder), schizophrenia and vascular dementia), for monitoring the effectiveness of treatment in these conditions and for use in drug development.

Other techniques such as magnetic resonance imaging or positron emission tomography based on subtle changes of the frontal and temporal lobes and the basal ganglia are of little value for the diagnosis, treatment, or prognosis of schizophrenic disorders in individual patients, since the absolute size of these reported differences between individuals with schizophrenia and normal comparison subjects has been generally small, with notable overlap between the two groups (16). The role of these neuroimaging techniques is restricted largely to the exclusion of other conditions which may be accompanied by schizophrenic symptoms, such as brain tumours or haemorrhages.

Therefore, a need exists to identify sensitive and specific biomarkers for differential diagnosis and for monitoring of schizophrenic disorders, bipolar disorders or of predisposition to a schizophrenic or bipolar disorder, in a living subject. Additionally, there is a clear need for methods, models, tests and tools for identification and assessment of existing and new therapeutic agents for the treatment of these conditions.

The VGF gene encodes a neuropeptide precursor which is expressed in a subset of neurons in the central and peripheral nervous system and in specific populations of endocrine cells found in the adenohypophysis, adrenal medulla, gastrointestinal tract and pancreas. Expression of VGF is upregulated in responsive neurons by neurotrophins. VGF is a recognised nerve growth factor and plays an essential role in the regulation of energy homeostasis. The human VGF protein is 615 amino acids in length; the VGF protein in mouse and rat is 617 amino acids in length. There is about 85% homology between the human and rat VGF proteins. The VGF neuropeptide precursor has a secretory leader ("signal") sequence of 22 amino acids that promotes translocation into the endoplasmic reticulum. In the VGF neuropeptide precursor and the mature full length VGF peptide cleaved from that precursor, there are numerous short stretches of basic amino acid residues, which are potential target sites for peptidase cleavage resulting in the generation of shorter VGF peptides. VGF peptides have been identified in rat and human; Stark et al (2001) (17) identified three N-terminal fragments of VGF (amino acids 23 to 62, 26 to 62 (N-terminal truncation of peptide 23 to 62) and 23 to 59 (C-terminal truncation of peptide 23 to 62)) in human cerebrospinal fluid (CSF) obtained from subjects without known neurological disorders.

VGF peptide biomarkers have been associated with chronic dementia diseases. International Patent Application No PCT/DE02/01376 (WO 02/082075) describes methods for detecting chronic dementia diseases, in particular Alzheimer's disease, involving detection of various VGF-derived peptides, including VGF 23 to 62 and VGF 26 to 62. These diseases are organic disorders. Diagnosis of a chronic dementia disease, such as those described in WO 02/082075, automatically excludes diagnosis of a schizophrenic or bipolar disorder. Until now, there has been no report of a VGF peptide associated with a schizophrenic disorder, bipolar disorder or predisposition thereto.

BRIEF DESCRIPTION OF THE SEQUENCES

SEQ ID NO: 1 is an amino acid sequence of a VGF peptide of the subject invention.

SEQ ID NO: 2 is an amino acid sequence of the native, full length human VGF peptide.

SEQ ID NO: 3 is an amino acid sequence of a VGF peptide.

STATEMENT OF INVENTION

The present invention provides the use of a VGF peptide, preferably consisting of the amino acid sequence shown in SEQ ID NO: 1, or a fragment thereof, as a biomarker for a schizophrenic disorder, bipolar disorder, or predisposition thereto.

The invention further provides a VGF peptide biomarker for a schizophrenic disorder, bipolar disorder, or predisposition thereto, preferably consisting of the amino acid sequence shown in SEQ ID NO: 1, or a fragment thereof.

The term "biomarker" means a distinctive biological or biologically derived indicator of a process, event, or condition. Biomarker peptides can be used in methods of diagnosis, e.g. clinical screening, and prognosis assessment; and in monitoring the results of therapy, identifying patients most likely to respond to a particular therapeutic treatment, drug screening and development. Biomarkers and uses thereof are valuable for identification of new drug treatments and for discovery of new targets for drug treatment.

The term "VGF peptide biomarker" includes the mature full length human VGF peptide generated by cleavage of the signal sequence from the human VGF neuropeptide precursor. Preferred VGF peptide biomarkers are peptides in which the N-terminus is generated by proteolytic cleavage of the putative secretory leader ("signal") sequence of the human VGF neuropeptide precursor. A particularly preferred VGF peptide biomarker (SEQ ID NO: 1) is derived from the human VGF and consists of amino acids 23 to 62 of human VGF. This biomarker amino acid sequence is found immediately following the carboxyl terminus of the putative signal peptide in human VGF protein (FIG. 3). The biomarker peptide as shown in SEQ ID NO: 1 (FIG. 2) is found to be present at elevated levels in individuals with first onset psychosis characteristic of schizophrenic or bipolar disorders, it is thus useful as a marker for diagnosing and monitoring schizophrenic disorders, bipolar disorder or predisposition thereto.

In a further aspect, the invention provides a method of diagnosing or monitoring a schizophrenic disorder, bipolar disorder, or predisposition thereto, comprising detecting and/or quantifying a VGF peptide biomarker, preferably consisting of the amino acid sequence of SEQ ID NO: 1, or a fragment thereof present in a biological sample from a test subject.

Monitoring methods of the invention can be used to monitor onset, progression, stabilisation, amelioration and/or remission of a schizophrenic disorder, bipolar disorder, or a predisposition thereto.

In methods of diagnosing or monitoring according to the invention, detecting and/or quantifying the biomarker peptide in a biological sample from a test subject may be performed on two or more occasions. Comparisons may be made between the level of biomarker in samples taken on two or more occasions. Assessment of any change in the level of biomarker peptide in samples taken on two or more occasions may be performed. Modulation of the biomarker peptide level is useful as an indicator of the state of the schizophrenic or bipolar disorder or predisposition thereto. An increase in the level of biomarker peptide over time is indicative of onset or progression, i.e. worsening of this disorder, whereas a decrease in the level of biomarker peptide indicates amelioration or remission of the disorder.

A method of diagnosis of or monitoring according to the invention may comprise quantifying a VGF peptide biomarker, preferably consisting of the amino acid sequence of SEQ ID NO: 1, or a fragment thereof in a test biological sample from a test subject and comparing the level of peptide present in said test sample with one or more controls.

The control used in a method of the invention can be one or more control(s) selected from the group consisting of: the level of biomarker found in a normal control sample from a normal subject, a normal biomarker level; a normal biomarker range; the level in a sample from a subject with a schizophrenic disorder, or bipolar disorder or a diagnosed predisposition thereto, or a schizophrenic disorder marker level, or bipolar disorder marker level; a schizophrenic disorder marker range and a bipolar disorder marker range.

A preferred method of diagnosing a schizophrenic disorder, bipolar disorder, or predisposition thereto, comprises:

(a) quantifying the amount of a VGF peptide biomarker, preferably consisting of SEQ ID NO: 1, or a fragment thereof in a test biological sample, (b) comparing the amount of said peptide in said test sample with the amount present in a normal control biological sample from a normal subject.

A higher level of the VGF biomarker peptide in the test sample relative to the normal control is indicative of a schizophrenic disorder, bipolar disorder, or predisposition thereto. An equivalent or lower level of said peptide in the test sample relative to the normal control is indicative of absence of a schizophrenic disorder, absence of a bipolar disorder, and/or absence of a predisposition thereto.

The term "diagnosis" as used herein encompasses identification, confirmation, and/or characterisation of a schizophrenic disorder, bipolar disorder, or predisposition to a schizophrenic disorder, or predisposition to a bipolar disorder. By predisposition it is meant that a subject does not currently present with the disorder, but is liable to be affected by the disorder in time. Methods of monitoring and of diagnosis according to the invention are useful to confirm the existence of a schizophrenic disorder, bipolar disorder, or predisposition thereto; to monitor development of the disorder by assessing onset and progression, or to assess amelioration or regression. Methods of monitoring and of diagnosis are also useful in methods for assessment of clinical screening, prognosis, choice of therapy, evaluation of therapeutic benefit, i.e. for drug screening and drug development in the field of schizophrenic disorder, bipolar disorder or a predisposition to a schizophrenic disorder or bipolar disorder.

Efficient diagnosis and monitoring methods provide very powerful 'patient solutions' with the potential for improved prognosis, by establishing the correct diagnosis, allowing rapid identification of the most appropriate treatment (thus lessening unnecessary exposure to harmful drug side effects), reducing 'down-time' and relapse rates.

Also provided is a method of monitoring efficacy of a therapy for a schizophrenic or bipolar disorder in a subject having such a disorder, suspected of having such a disorder or of being predisposed thereto, comprising detecting and/or quantifying a VGF peptide, preferably consisting of the amino acid sequence of SEQ ID NO: 1, or a fragment thereof in a biological sample from said subject. In monitoring methods, test samples may be taken on two or more occasions. The method may further comprise comparing the level of the biomarker present in the test sample with one or more control and/or with one or more previous test samples taken earlier from the same test subject, e.g. prior to commencement of therapy, and/or from the same test subject, at an earlier stage of therapy. The method may comprise detecting a change in the level of the biomarker in test samples taken on different occasions.

The invention thus provides a method for monitoring efficacy of therapy for a schizophrenia or bipolar disorder in a subject, comprising:

(a) quantifying the amount of a VGF peptide biomarker, preferably consisting of the amino acid sequence of SEQ ID NO: 1 or a fragment thereof in a test biological sample taken from said subject, (b) comparing the amount of said peptide in said test sample with the amount present in one or more controls and/or one or more previous test samples taken at an earlier time from said same test subject.

A decrease in the level of the biomarker peptide in the test sample relative to a previous test sample taken earlier from the same test subject is indicative of a beneficial effect, e.g. stabilisation or improvement, of said therapy on the disorder, suspected disorder or predisposition thereto.

Methods for monitoring efficacy of a therapy can be used to monitor the therapeutic effectiveness of existing therapies and new therapies in human subjects and in non-human animals (e.g. in animal models). These monitoring methods can be incorporated into screens for new drug substances and combinations of substances.

Suitably, the time elapsed between taking samples from a subject undergoing diagnosis or monitoring will be 3 days, 5 days, a week, two weeks, a month, 2 months, 3 months, 6 or 12 months. Samples may be taken prior to and/or during and/or following an anti-schizophrenic or anti-bipolar disorder therapy. Samples can be taken at intervals over the remaining life, or a part thereof, of a subject.

The term "detecting" as used herein means confirming the presence of a VGF biomarker peptide, preferably consisting of the amino acid sequence of SEQ ID NO: 1 or a fragment thereof present in the sample. Quantifying the amount of the biomarker present in a sample may include determining the concentration of the biomarker peptide present in the sample. Detecting and/or quantifying may be performed directly on the sample, or indirectly on an extract therefrom, or on a dilution thereof.

In alternative aspects of the invention, the presence of the biomarker peptide is assessed by detecting and/or quantifying antibody or fragments thereof capable of specific binding to the biomarker that are generated by the subject's body in response to the peptide and thus are present in a biological sample from a subject having a schizophrenic or bipolar disorder.

Detecting and/or quantifying can be performed by any method suitable to identify the presence and/or amount of a specific protein in a biological sample from a patient or a purification of extract of a biological sample or a dilution thereof. In methods of the invention, quantifying may be performed by measuring the concentration of the VGF biomarker peptide in the sample or samples. Biological samples that may be tested in a method of the invention include cerebrospinal fluid (CSF), whole blood, blood serum, urine, saliva, or other bodily fluid (stool, tear fluid, synovial fluid, sputum), breath, e.g. as condensed breath, or an extract or purification therefrom, or dilution thereof. Biological samples also include tissue homogenates, tissue sections and biopsy specimens from a live subject, or taken postmortem. The samples can be prepared, for example where appropriate diluted or concentrated, and stored in the usual manner.

Detection and/or quantification of VGF biomarker peptides may be performed by detection of the biomarker peptide or of a fragment thereof, e.g. a fragment with C-terminal truncation, or with N-terminal truncation. Fragments are suitably greater than 4 amino acids in length.

The biomarker may be directly detected, e.g. by SELDI, MALDI-TOF. Alternatively, the biomarker may be detected directly or indirectly via interaction with a ligand or ligands such as an antibody or a biomarker-binding fragment thereof, or other peptide, or ligand, e.g. aptamer or oligonucleotide, capable of specifically binding the biomarker. The ligand may possess a detectable label, such as a luminescent, fluorescent or radioactive label, or an affinity tag.

For example, detecting and/or quantifying can be performed by one or more methods selected from the group consisting of: SELDI (-TOF) and/or MALDI (-TOF), a 1-D gel-based analysis, a 2-D gel-based analysis, Mass spec (MS) and LC-MS-based techniques. Appropriate LC MS techniques include ICAT® (Applied Biosystems, CA, USA), or iTRAQ® (Applied Biosystems, CA, USA). Liquid chromatography (e.g. high pressure liquid chromatography (HPLC) or low pressure liquid chromatography (LPLC)), thin-layer chromatography, NMR (nuclear magnetic resonance) spectroscopy could also be used.

Methods for diagnosis or monitoring according to the invention may comprise analysing a sample of cerebrospinal fluid (CSF) by SELDI TOF or MALDI TOF to detect the presence or level of the Biomarker peptide of SEQ ID NO: 1 (3.96 kDa, with a calibration associated error=2%) (FIG. 1). These methods are also suitable for clinical screening, prognosis, monitoring the results of therapy, identifying patients most likely to respond to a particular therapeutic treatment, for drug screening and development, and identification of new targets for drug treatment.

Detecting and/or quantifying the VGF peptide biomarker may be performed using an immunological method, involving an antibody, or a fragment thereof capable of specific binding to the VGF peptide biomarker, e.g. to a peptide consisting of the amino acid sequence shown in SEQ ID NO: 1 or a fragment thereof. Suitable immunological methods include sandwich immunoassays, such as sandwich ELISA in which the detection of the biomarker peptides is performed using two antibodies which recognize different epitopes on the biomarker peptide; radioimmunoassays (RIA), direct or competitive enzyme linked immunosorbent assays (ELISA), enzyme immuno assays (EIA), western blotting, immunoprecipitation and any particle-based immunoassay (e.g. using gold, silver, or latex particles, magnetic particles, or Q-dots). Immunological methods may be performed, for example, in microtitre plate or strip format.

The term "antibody" as used herein includes, but is not limited to: polyclonal, monoclonal, bispecific, humanised or chimeric antibodies, single chain antibodies, Fab fragments and F (ab')$_2$ fragments, fragments produced by a Fab expression library, anti-idiotypic (anti-Id) antibodies, and epitope-binding fragments of any of the above. The term "antibody" as used herein also refers to immunoglobulin molecules and immunologically-active portions of immunoglobulin molecules, i.e., molecules that contain an antigen binding site that specifically binds an antigen. The immunoglobulin molecules of the invention can be of any class (e.g., IgG, IgE, IgM, IgD and IgA) or subclass of immunoglobulin molecule.

The identification of key biomarkers specific to a disease is central to integration of diagnostic procedures and therapeutic regimes. Using predictive biomarkers appropriate diagnostic tools such as biosensors can be developed, accordingly, in methods and uses of the invention, detecting and quantifying can be performed using a biosensor. The biosensor may incorporate an immunological method for detection of the biomarker, an electrical, thermal, magnetic, optical (e.g. hologram) or acoustic technologies. Using such biosensors, it is possible to detect the target biomarker at the anticipated concentrations found in biological samples.

The biomarker of the invention can be detected using a biosensor incorporating technologies based on "smart" holograms, or high frequency acoustic systems, such systems are particularly amenable to "bar code" or array configurations.

In smart hologram sensors (Smart Holograms Ltd, Cambridge, UK), a holographic image is stored in a thin polymer film that is sensitised to react specifically with the biomarker. On exposure, the biomarker reacts with the polymer leading to an alteration in the image displayed by the hologram. The test result read-out can be a change in the optical brightness, image, colour and/or position of the image. For qualitative and semi-quantitative applications, a sensor hologram can be read by eye, thus removing the need for detection equipment, A simple colour sensor can be used to read the signal when quantitative measurements are required. Opacity or colour of the sample does not interfere with operation of the sensor. The format of the sensor allows multiplexing for simultaneous detection of several substances. Reversible and irreversible sensors can be designed to meet different requirements, and continuous monitoring of a particular biomarker of interest is feasible.

Suitably, biosensors for detection of the biomarker of the invention combine biomolecular recognition with appropriate means to convert detection of the presence, or quantitation, of the biomarker in the sample into a signal. Biosensors can be adapted for "alternate site" diagnostic testing, e.g. in the ward, outpatients' department, surgery, home, field and workplace.

Biosensors to detect the biomarker of the invention include acoustic, plasmon resonance, holographic and microengineered sensors. Imprinted recognition elements, thin film transistor technology, magnetic acoustic resonator devices and other novel acousto-electrical systems may be employed in biosensors for detection of the biomarkers of the invention.

Methods involving detection and/or quantification of the biomarker peptide of the invention can be performed on bench-top instruments, or can be incorporated onto disposable, diagnostic or monitoring platforms that can be used in a non-laboratory environment, e.g. in the physician's office or at the patients bedside. Suitable biosensors for performing methods of the invention include "credit" cards with optical or acoustic readers. Biosensors can be configured to allow the data collected to be electronically transmitted to the physician for interpretation and thus can form the basis for e-neuro-medicine.

In methods and uses of the invention in which the amount of the VGF biomarker peptide of SEQ ID NO: 1 or a fragment thereof present in a test sample from a test subject is measured, detection of a higher level of the biomarker peptide in the test sample compared to the level found in a normal control sample from a normal individual is indicative of a schizophrenic disorder, bipolar disorder or a predisposition thereto in the test subject. For example, the level of peptide of SEQ ID NO: 1 detected in a sample from a test subject with a schizophrenic disorder, bipolar disorder or predisposition thereto will generally be greater than 2.5-fold or higher, e.g. about 2.8-fold or higher, than the amount of the peptide found in a normal control sample. Expressed as a ratio, a higher level of peptide of SEQ ID NO: 1 indicative of a schizophrenic disorder, bipolar disorder or a predisposition thereto exists when the ratio of the amount of peptide of SEQ ID NO: 1 in a test sample compared to a normal control is 1:2.5 or higher, e.g. 1:2.8 or higher.

A further aspect of the invention provides ligands, such as naturally occurring or chemically synthesised compounds, capable of specific binding to the VGF peptide biomarker. A ligand according to the invention may comprise a peptide, an antibody or a fragment thereof, or an aptamer or oligonucleotide, capable of specific binding to the VGF peptide biomarker. The antibody can be a monoclonal antibody or a fragment thereof capable of specific binding to the VGF peptide biomarker. A ligand according to the invention may be labelled with a detectable marker, such as a luminescent, fluorescent or radioactive marker; alternatively or additionally a ligand according to the invention may be labelled with an affinity tag.

Biosensors according to the invention may comprise a ligand or ligands, as described herein, capable of specific binding to the VGF peptide biomarker. Such biosensors are useful in detecting and/or quantifying a peptide of the invention.

A biosensor according to the invention may comprise the VGF peptide biomarker, or a structural/shape mimic thereof capable of specific binding to an antibody against the VGF peptide biomarker.

Also provided is an array comprising a ligand as described herein capable of specific binding to the VGF peptide biomarker, or an array comprising the VGF peptide biomarker or a structural/shape mimic thereof.

Diagnostic or monitoring kits are provided for performing methods of the invention. Such kits will suitably comprise a ligand according to the invention, for detection and quantification of the VGF peptide biomarker, and/or a biosensor, and/or an array as described herein, optionally together with instructions for use of the kit.

Also provided by the invention is the use of a ligand as described herein, which may be naturally occurring or chemically synthesised, and is suitably a peptide, antibody or fragment thereof, aptamer or oligonucleotide, or the use of a biosensor of the invention, or an array of the invention, or a kit of the invention, to detect and/or quantify the VGF peptide biomarker or a fragment thereof. In this use, the detection and/or quantification can be performed on a biological sample such as from the group consisting of CSF, whole blood, blood serum, urine, saliva, or other bodily fluid, breath, e.g. as condensed breath, or an extract or purification therefrom, or dilution thereof.

Biomarkers for schizophrenic disorders or bipolar affective disorder are essential targets for discovery of novel targets and drug molecules that retard or halt disease progression. As the level of a VGF biomarker peptide is indicative of disorder and of drug response, the biomarker is useful for identification of novel therapeutic compounds in in vitro and/or in vivo assays. The biomarker of the invention can be employed in methods for screening for compounds that modulate the activity of, or suppress the generation of, a VGF peptide biomarker according to the invention.

Thus, in a further aspect of the invention, there is provided the use of a ligand, as described, which can be a peptide, antibody or fragment thereof or aptamer or oligonucleotide according to the invention; or the use of a biosensor according to the invention, or an array according to the invention; or a kit according to the invention, to identify a substance capable of suppressing the generation of a VGF peptide biomarker.

Accordingly there is provided a method of identifying a substance capable of suppressing the generation of a VGF peptide biomarker, the VGF peptide biomarker preferably consisting of the amino acid sequence of SEQ ID NO: 1, or a fragment thereof, in a subject, comprising administering a test substance to a subject animal and detecting and/or quantifying levels of the peptide present in a test sample from the subject.

Any suitable animal may be used as a subject non-human animal, for example a non-human primate, horse, cow, pig, goat, sheep, dog, cat, fish, rodent, e.g. guinea pig, rat or mouse; insect (e.g. *Drosophila*), amphibian (e.g. *Xenopus*) or *C. elegans*.

The test substance can be a known chemical or pharmaceutical substance, such as, but not limited to, an anti-schizophrenic or anti-bipolar disorder therapeutic, e.g. a known anti-psychotic; or the test substance can be novel synthetic or natural chemical entity, or a combination of two or more of the aforesaid substances.

There is provided a method of identifying a substance capable of suppressing the generation of a VGF biomarker peptide, preferably consisting of the amino acid sequence of SEQ ID NO: 1, or a fragment thereof in a subject, comprising exposing a test cell to a test substance and monitoring levels of the VGF peptide biomarker within said test cell, or secreted by said test cell. The test cell could be prokaryotic, however it is preferred that a eukaryotic cell be employed in cell-based testing methods. Suitably, the eukaryotic cell is a yeast cell, insect cell, *Drosophila* cell, amphibian cell (e.g. from *Xenopus*), *C. elegans* cell or is a cell of human, non-human primate, equine, bovine, porcine, caprine, ovine, canine, feline, piscine, rodent or murine origin.

In methods for identifying substances of potential therapeutic use, non-human animals or cells can be used that are capable of expressing one or more polypeptide selected from the group consisting of human VGF polypeptides and proteolytic enzymes, preferably human proteolytic enzymes capable of cleaving a human VGF polypeptide.

Screening methods also encompass a method of identifying a ligand capable of binding to a VGF biomarker peptide according to the invention, comprising incubating a test substance in the presence of the biomarker peptide in conditions appropriate for binding, and detecting and/or quantifying binding of the peptide to said test substance.

Where the VGF biomarker peptide is a peptide consisting of the sequence of SEQ ID NO: 1 (human VGF amino acids 23 to 62), or a fragment thereof specific binding is indicated if the test substance does not bind to human VGF protein or to a protein consisting of amino acids 26 to 62 of human VGF (N-terminal 3 peptide truncated sequence).

High-throughput screening technologies based on the biomarker, uses and methods of the invention, e.g. configured in an array format, are suitable to monitor biomarker signatures for the identification of potentially useful therapeutic compounds, e.g. ligands such as natural compounds, synthetic chemical compounds (e.g. from combinatorial libraries) peptides, monoclonal or polyclonal antibodies or fragments thereof capable of binding the biomarker.

Methods of the invention can be performed in array format, e.g. on a chip, or as a multiwell array. Methods can be adapted into platforms for single tests, or multiple identical or multiple non-identical tests, and can be performed in high throughput format. Methods of the invention may comprise performing one or more additional, different tests to confirm or exclude diagnosis, and/or to further characterise a condition.

The invention further provides a substance, e.g. a ligand, identified or identifiable by an identification or screening method or use of the invention. Such substances may be capable of inhibiting, directly or indirectly, the activity of a VGF biomarker peptide, or of suppressing generation of the VGF biomarker peptide. The term substances includes inhibitory substances that do not directly bind the VGF biomarker peptide and directly inhibit a function, but instead indirectly inhibit a function of the VGF biomarker peptide. Ligands are also included in the term substances, ligands of the invention (e.g. a natural or synthetic chemical compound, peptide, aptamer, oligonucleotide, antibody or antibody fragment) are capable of binding, preferably specific binding, to a VGF biomarker peptide.

The invention further provides the use of a substance or ligand according to the invention in the treatment of a schizophrenic disorder, bipolar disorder, or predisposition thereto.

Also provided is the use of a substance according to the invention as a medicament.

Yet further provided is the use of a substance according to the invention in the manufacture of a medicament for the treatment of a schizophrenic disorder, bipolar disorder, or predisposition thereto.

A kit for diagnosing or monitoring a schizophrenic disorder, bipolar disorder or predisposition thereto is provided. Suitably a kit according to the invention may contain one or more components selected from the group: a ligand specific for a VGF peptide biomarker, a VGF peptide biomarker or a structural/shape mimic of a VGF peptide biomarker, a control(s), a reagent(s), and a consumable(s); optionally together with instructions for use of the kit.

The identification of biomarkers for schizophrenic disorders and bipolar disorders permits integration of diagnostic procedures and therapeutic regimes. Currently there are significant delays in determining effective treatment and it has not hitherto been possible to perform rapid assessment of drug response. Traditionally, many anti-schizophrenic and bipolar disorder therapies have required treatment trials lasting weeks to months for a given therapeutic approach. Detection of a VGF biomarker of the invention can be used to screen subjects prior to their participation in clinical trials. The biomarker provides a means to indicate therapeutic response, failure to respond, unfavourable side-effect profile, degree of medication compliance and adequate serum drug levels. The biomarker may be used to provide warning of adverse drug response, a major problem encountered with all psychotropic medications. Biomarkers are useful in development of personalized brain therapies, as assessment of response can be used to fine-tune dosage, minimise the number of prescribed medications, reduce the delay in attaining effective therapy and avoid adverse drug reactions. Thus by monitoring a biomarker of the invention, patient care can be tailored precisely to match the needs determined by the disorder and the pharmacogenomic profile of the patient, the biomarker can thus be used to titrate the optimal dose, predict a positive therapeutic response and identify those patients at high risk of severe side effects.

Biomarker based tests provide a first line assessment of 'new' patients, and provide objective measures for accurate and rapid diagnosis, in a time frame and with precision not achievable using the current subjective measures. The biomarker of the invention permits differential diagnosis of schizophrenia and bipolar disorders over other disorders and conditions that present with similar or overlapping symptoms.

Furthermore, diagnostic biomarker tests are useful to identify family members or patients in the "prodromal phase", i.e. those at high risk of developing overt schizophrenia or bipolar disorder. This permits initiation of appropriate therapy, for example low dose antipsychotics, or preventive measures, e.g. managing risk factors such as stress, illicit drug use or viral infections. These approaches are recognised to improve outcome and may prevent overt onset of the disorder.

Biomarker monitoring methods, biosensors and kits are also vital as patient monitoring tools, to enable the physician to determine whether relapse is due to a genuine breakthrough or worsening of the disease, poor patient compliance or substance abuse. As the biomarker is sensitive to the state of the disorder it provides an indication of the impact of drug therapy or of substance abuse. If pharmacological treatment is assessed to be inadequate, then therapy can be reinstated or increased. For genuine breakthrough disease, a change in therapy can be given if appropriate. Biomarker tests of the invention enable psychotic episodes induced by substance abuse, to be distinguished from relapses of a schizophrenic or bipolar disorder. Using the current techniques for assessment, diagnosis may be incorrect and suggest therapy by short-term symptomatic antipsychotic use, which is inappropriate in drug-induced psychosis, a condition that is self-limiting and subsides on wash-out of the illicit substance. The biomarker of the present invention thus provides means for accurate diagnosis and therapeutic intervention in schizophrenic disorders, bipolar disorder and predisposition thereto.

BRIEF DESCRIPTION OF THE FIGURES

FIG. 1C shows the relative intensity of the 3.96 kDa peak in healthy volunteers and in patients with first onset psychosis.

FIG. 3. Mapping the biomarker peptide to VGF protein.

A. The peptide of 3.96 kDa (or 3.95 kDa from ESI-MS/MS spectrum) was mapped to amino acids 23 to 62 (SEQ. ID NO: 1: in bold underlined) of the native VGF protein (SEQ ID NO: 2), immediately next to a predicted secretory signal peptide (using InterProScan: European Bioinformatics Institute). This 3.96 kDa peptide has the amino acid sequence shown in SEQ ID NO: 1.

B. Sequence alignment of the 3.96 kDa peptide and the 3.69 kDa peptide. De novo sequencing using ES/MS-MS showed that the 3.69 kDa peptide (SEQ ID NO: 3) in the CSF is a three amino acid (at the N-terminus) shorter form of the 3.96 kDa peptide (data not shown), which is not differentially expressed in CSF (p=0.87) from healthy volunteers and patients with first onset psychosis. This indicates that the 3.96 kDa VGF peptide is highly specific to conditions that present with first onset psychosis, i.e. schizophrenic and/or bipolar disorders.

Figure 1:
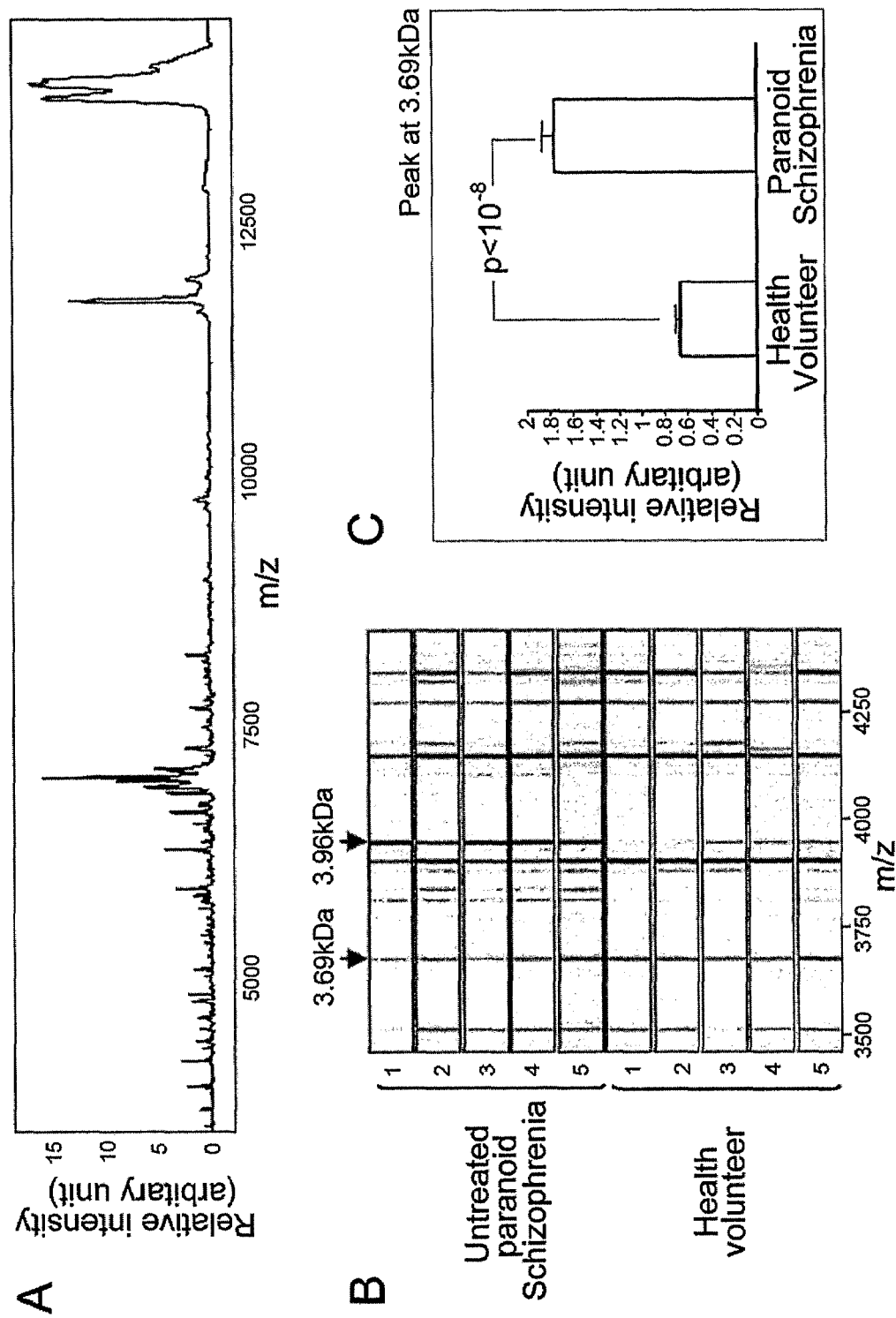
FIG. 1. A schizophrenia specific biomarker (a peptide of SEQ ID NO: 1) in CSF at 3.96 kDa. Cerebrospinal fluid (CSF) samples from 40 healthy volunteers and from 40 untreated subjects with first onset psychosis (which can develop into a schizophrenic or bipolar disorder) were included in this study. An aliquot of 5 µl of each CSF sample was applied to each of the protein chips tested (each having different chemical properties) at various pH conditions. The best conditions were found to be at pH 9.0 on strong anion exchanger Q10 chip, the selection of these parameters was based on the number and separation of peaks resolved. The protein/peptides bound to the chip surface were then analysed by SELDI mass spectrometry. An example of a spectrum from a healthy volunteer is shown in FIG. 1A. The intensities of the peaks in each spectrum were collected and analysed using ProteinChip™ software (Ciphergen, Fremont, USA). An increase in the peak at 3.96 kDa was observed (as shown in FIG. 1B). No difference was found at the 3.69 kDa peak, a three amino acid shorter form (at the N-terminus) of the peptide that constitutes the 3.96 kDa peak (see FIG. 3B, sequencing data not shown).
Figure 2:
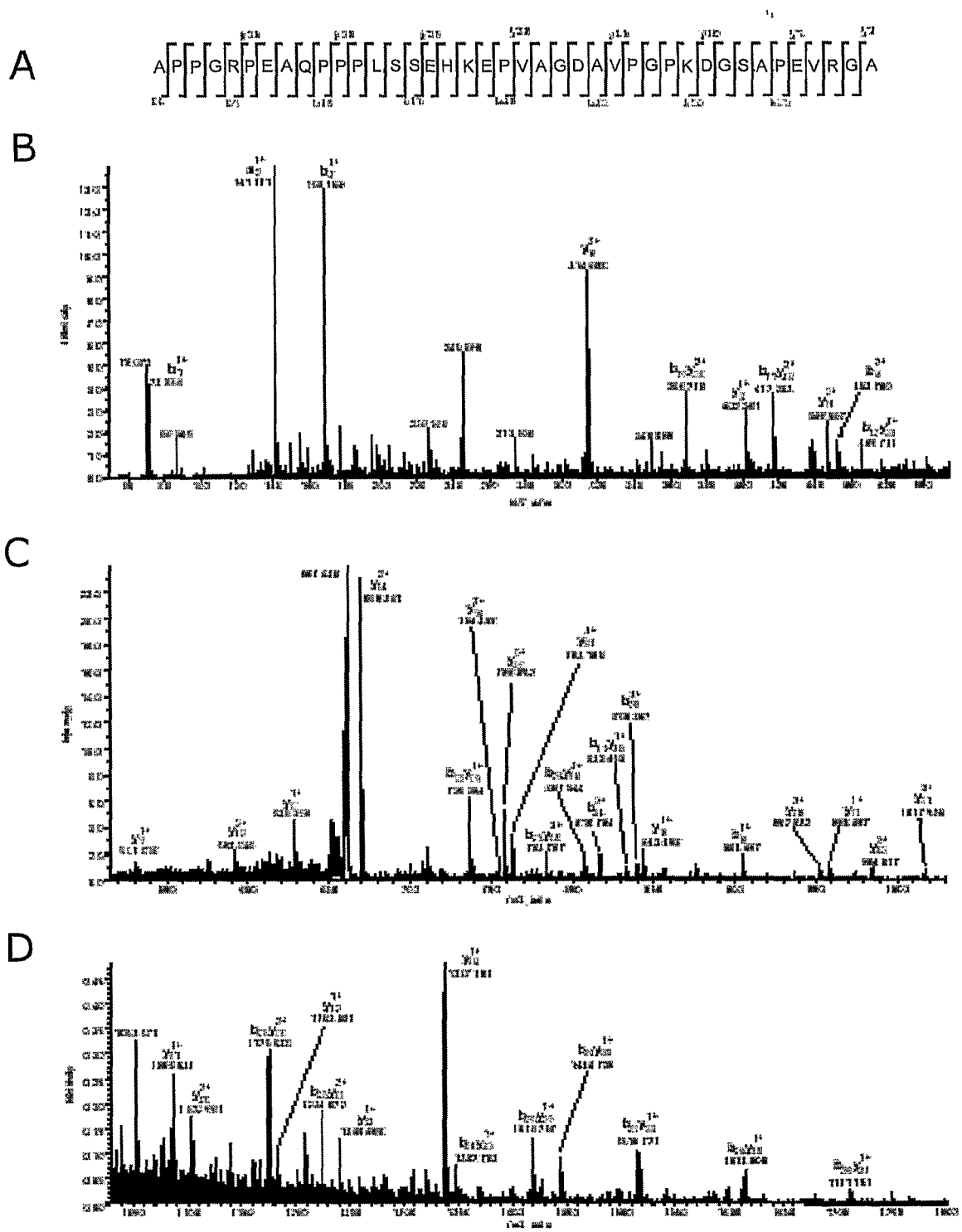
FIG. 2. Identification of the 3.96 kDa peptide of SEQ ID NO: 1 as a VGF peptide fragment. Samples of 50 µl of the CSFs with highest expression of 3.96 kDa peak were processed with 10 kDa cut-off column to remove large proteins. The flow-through was then desalted using a C18 Ziptip (Millipore, Billericak, USA) and the peptides were eluted with 0.1% formic acid/50% aqueous acetonitrile. Aliquots of 1 µl of the eluate were loaded directly into a nanospray tip for ESI-MS/MS (for de novo sequencing) and SELDI mass spectrometers (for the confirmation of the enriched 3.96 kDa peak). The 3.96 kDa peak in the SELDI spectrum was matched to the 3.95 peptide (m/z 659.9 (approximate mass) in the 6+ charge state. MS/MS spectrum of this peptide is shown in FIG. 2B-D. Assigned prominent ions, together with their respective charge states are labelled. These are predominantly y and 6 series ions, as well as ions arising from double fragmentations (labelled as by ions). For clarity, secondary fragment ions arising from the loss of water or ammonia are not labelled, FIG. 2A shows the amino acid sequence derived from the MS/MS spectrum.
Figure 4:
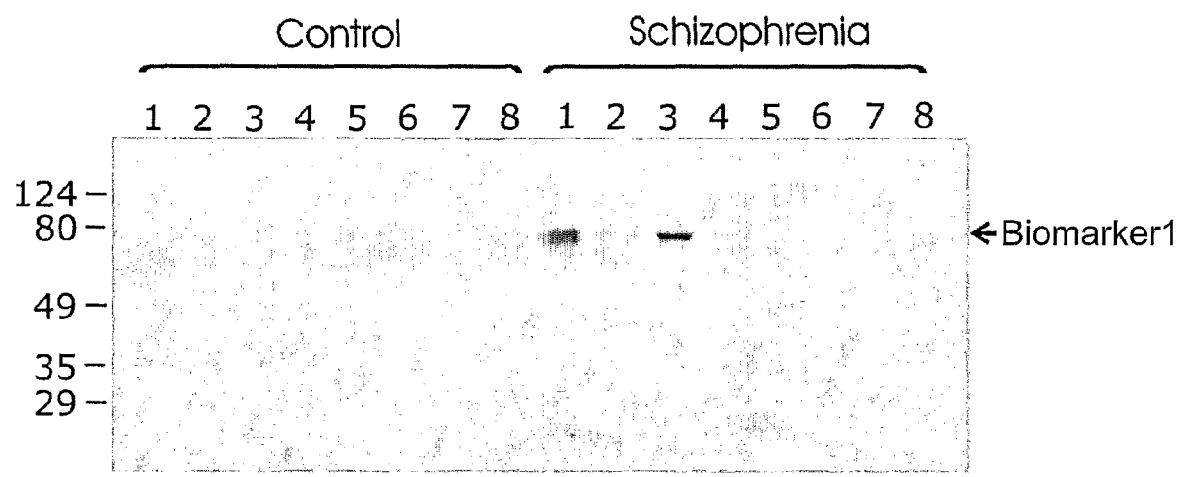

FIG. 4. Western blotting analysis of mature full length human VGF peptide biomarker in the prefrontal cortex of age-matched controls and patients with schizophrenia.

EXAMPLES

Materials

Age-matched CSF samples were obtained from healthy individuals (n=40) and patients with first onset psychosis with prominent symptoms of schizophrenia/bipolar disorder (drug free) (n=40). All chemicals were obtained from Sigma. Protein chips and matrices were obtained from Ciphergen (Guildford, UK).

Preparation of CSF Samples for SELDI Analysis.

Aliquots of 5 µl of the CSF samples were processed on strong anion-exchange (Q10) chips according to the manufacturer's protocols (Ciphergen Biosystems). Briefly, the array spots were preactivated twice with binding buffer (100 mM Tris-HCl, pH 9.0) at room temperature for 10 minutes on a shaker (frequency=5 Hz). Then, 50 µl of binding buffer was added into each protein spot prior to the addition of 5 µl CSF samples. The protein chips were incubated on the shaker for 30 minutes at room temperature. The chips were washed twice with binding buffer and once with HPLC grade $H_2O$, and then air-dried. The chips were then sequentially treated twice with 1 µl of a 100% saturated sinapinic acid (3,5-dimethoxy-4-hydroxycinnamic acid) in 50% acetonitrile and 0.5% trifluoroacetic acid. The chips were analyzed with the Ciphergen ProteinChip™ Reader (model PBSII). Each sample was analyzed twice to confirm reproducibility in identifying the differentially expressed proteins.

Ciphergen ProteinChip™ SELDI-TOF-MS Analysis.

The arrays were analyzed with the Ciphergen ProteinChip Reader (model PBSII). The mass spectra of proteins were generated by using an average of 65 laser shots at a laser intensity of 230-280 arbitrary units. For data acquisition of low molecular weight proteins, the detection size range was between 3 and 20 kDa, with a maximum size of 25 kDa. The laser was focused at 10 kDa. The detector sensitivity was set at 8, and the laser intensity was set at 190. For the high molecular weight proteins, the detection size range was between 20 and 150 kDa, with a maximum size of 250 kDa. The laser was focused at 85 kDa. The detector sensitivity was set at 9, and the laser intensity was set at 260 for the 1:4 dilution and 280. The mass-to-charge ratio (m/z) of each of the proteins captured on the array surface was determined according to externally calibrated standards (Ciphergen Biosystems): bovine insulin (5,733.6 Da), human ubiquitin (8,564.8 Da), bovine cytochrome c (12,230.9 Da), bovine superoxide dismutase (15,591.4 Da), bovine α-lactoglobulin A (18,363.3 Da), horseradish peroxidase (43,240 Da), BSA (66,410 Da), and chicken conalbumin (77,490 Da).

LC-MS-MS analysis of CSF Peptides.

Proteins were removed from a 50 µl sample of CSF using a Nanosep™ (Pall Corporation) centrifugal ultrafiltration device with a 10 kDa nominal molecular weight cut-off. An aliquot (5 µl) of the filtrate was desalted by solid-phase microextraction on a C18 ZipTip™ (Waters) and the peptides eluted with 0.1% formic acid/50% aqueous acetonitrile (1 µl) directly into a nanospray tip (Protana Engineering). The nanospray tip was inserted into a nanoelectrospray ion source (Protana Engineering) attached to a quadupole-time-of-flight mass spectrometer (Qstar Pulsar i, Applied Biosystems-MDS Sciex) and full scan TOF spectra were acquired for 5-10 minutes over the m/z range 350-1500 atomic mass units. MS/MS spectra were acquired over the m/z range 50-1700 atomic mass units until sufficient signal noise was attained. The collision energy was optimized during data acquisition to give the widest range of fragment ions.

MS/MS data were manually interpreted to extract "sequence tags" which were used with BioAnalyst™ software (Applied Biosystems) to search the NCBI NRDB database. The search results were confirmed by further manual interpretation of the MS/MS data.

Statistical Analysis.

The data were analyzed with PROTEINCHIP™ data analysis software version 3.0 (Ciphergen Biosystems). For each comparison, the raw intensity data were normalized by using the total ion current of all profiles in the groups compared. The peak intensities were normalized to the total ion current of m/z between 3,000 and 25,000 Da for the low molecular weight range and between 4,000 and 250,000 Da for the high molecular weight range. The Biomarker Wizard application (nonparametric calculations; Ciphergen Biosystems) was used to compile all spectra and autodetect quantified mass peaks. Peak labeling was completed by using second-pass peak selection with 0.2% of the mass window, and estimated peaks were added. Sample statistics were performed on groups of profiles (normal vs. first onset psychosis). Protein differences (fold changes) were calculated among the various groups.

VGF Peptide is Upregulated in the Prefrontal Cortex of Patients with Schizophrenia.

Eight schizophrenic and eight control brains (prefrontal cortex, matched for demographic variables) were selected at random. Western analysis was performed on extracts of postmortem brain tissue from pre-frontal cortex using a polyclonal antibody (Santa Cruz Biotechnology Inc., (VGF R-15): sc-10383; affinity purified goat polyclonal antibody raised against the carboxy terminus of VGF of rat origin). The VGF peptide biomarker (mature human VGF, without the signal peptide, FIG. 3A) was found to be significantly upregulated in 4 patients (out of 8 patients) with established schizophrenia compared to controls (FIG. 4). Similar results were obtained in an additional experiment (10 controls and 10 diagnosed cases of schizophrenia, data not shown). This result, together with the data from SELDI mass spectrum, indicates that the mature VGF peptide biomarker is associated with the pathogenesis of schizophrenia and therefore can be used as a diagnostic/prognostic marker and/or therapeutic target for schizophrenia.

REFERENCES

1. Thaker G K, Carpenter W T, Jr.: Advances in schizophrenia. *Nat Med* 7:667-671, 2001.
2. Susser E, Wanderling J: Epidemiology of noneffective acute remitting psychosis vs schizophrenia. Sex and sociocultural setting. *Arch Gen Psychiatry* 51:294-301, 1994,
3. Jablensky A: Epidemiology of schizophrenia: the global burden of disease and disability. *Eur Arch Psychiatry Clin Neurosci* 250:274-285, 2000.
4. Ustun T B: The global burden of mental disorders. *Am J Public Health* 89:1315-1318, 1999.

5. Johnstone E C, Crow T J, Johnson A L, MacMillan J F: The Northwick Park Study of first episodes of schizophrenia. I. Presentation of the illness and problems relating to admission. *Br J Psychiatry* 148:115-120, 1986.
6. APA: *Diagnostic and Statistical Manual of Mental Disorders*. Washington D.C., American Psychatric Association, 1994.
7. Loebel A D, Lieberman J A, Alvir J M, Mayerhoff D I, Geisler S H, Szymanski S R: Duration of psychosis and outcome in first-episode schizophrenia. *Am J Psychiatry* 149:1183-1188, 1992.
8. Wyatt R J: Neuroleptics and the natural course of schizophrenia. *Schizophr Bull* 17:325-351, 1991.
9. Fiedler P, Wolkin A, Rotrosen J: Niacin-induced flush as a measure of prostaglandin activity in alcoholics and schizophrenics. *Biol Psychiatry* 21:1347-1350, 1986.
10. Horrobin D F; Niacin flushing, prostaglandin E and evening primrose oil: a possible objective test for monitoring therapy in schizophrenia. *Orthomol. Psychiatry* 9:33-34, 1980.
11. Rybakowski J, Weterle R: Niacin test in schizophrenia and affective illness. *Biol Psychiatry* 29:834-836, 1991.
12. Puri B K, Hirsch S R, Easton T, Richardson A J: A volumetric biochemical niacin flush based index that non-invasively detects fatty acid deficiency in schizophrenia. *Prog Neuropsychopharmacol Biol Psychiatry* 26:49-52, 2002.
13. Tavares H, Yacubian J, Talib L L, Barbosa N R, Gattaz W F: Increased phospholipase A2 activity in schizophrenia with absent response to niacin. *Schizophr Res* 61:1-6, 2003.
14. Ward P E G, A.I.M.,: Niacin response and phospholipids in psychiatry. *World J. Biol. Psychiatry* 2: 296, 2001.
15. Weterle R, Rybakowski J: [The niacin test in schizophrenia]. *Psychiatr Pol* 24:116-120, 1990.
16. McNeil T F, Cantor-Graae E, Weinberger D R: Relationship of Obstetric Complications and Differences in Size of Brain Structures in Monozygotic Twin Pairs Discordant for Schizophrenia. *Am J Psychiatry* 157:203-212, 2000.
17. Stark M, Danielsson O, Griffiths W J, Jörnvall H, Johansson J: Peptide repertoire of human cerebrospinal fluid: novel proteolytic fragments of neuroendocrine proteins. *J. Chromatography B,* 754, 357-367, 2001.

---

The invention claimed is:

1. A method of diagnosing a schizophrenic disorder, or predisposition thereto, comprising:
   (a) quantifying an amount of a VGF biomarker peptide consisting of SEQ ID NO:1 present in a test CSF sample from a test subject; and
   (b) comparing the amount of the VGF biomarker peptide in said test sample with an amount of the VGF biomarker peptide present in a normal control CSF sample from a normal subject;

wherein a higher level of the VGF biomarker peptide in the test CSF sample is indicative of a schizophrenic disorder, or predisposition thereto, in the test subject.

2. The method according to claim 1, wherein step (a) additionally comprises quantifying the VGF peptide biomarker consisting of the amino acid sequence of SEQ ID NO:1 present in CSF samples taken on one or more further occasions from the test subject.

3. The method according to claim 2, further comprising comparing the level of the VGF peptide biomarker present in samples taken on said one or more further occasions.

4. The method according to claim 1, wherein the test CSF samples are taken at intervals over the remaining life, or a part thereof, of the subject.

5. The method according to claim 1, wherein quantifying is performed by measuring the concentration of the VGF biomarker peptide in said sample(s).

6. The method according to claim 1, wherein quantifying is performed by one or more methods selected from the group consisting of: SELDI (-TOF) and/or MALDI (-TOF), a 1-D gel-based analysis, a 2-D gel-based analysis, Mass spec (MS) and LC-MS-based techniques.

7. The method according to claim 1, wherein quantifying is performed using an immunological method.

8. The method according to claim 1, wherein quantifying, is performed using a biosensor.

9. The method according to claim 1 performed in chip, array and/or multiwell array format.

10. The method according to claim 1 performed in high throughput format.

* * * * *

UNITED STATES PATENT AND TRADEMARK OFFICE
CERTIFICATE OF CORRECTION

| | | |
|---|---|---|
| PATENT NO. | : 7,838,246 B2 | Page 1 of 1 |
| APPLICATION NO. | : 11/813122 | |
| DATED | : November 23, 2010 | |
| INVENTOR(S) | : Sabine Bahn et al. | |

It is certified that error appears in the above-identified patent and that said Letters Patent is hereby corrected as shown below:

<u>Column 14,</u>
Line 31, "thereof specific" should read --thereof, specific--

<u>Column 16,</u>
Line 50, "y and 6 series" should read --$y$ and $b$ series--

Signed and Sealed this
First Day of March, 2011

David J. Kappos
*Director of the United States Patent and Trademark Office*